United States Patent [19]

Aizawa et al.

[11] Patent Number: 5,300,606

[45] Date of Patent: * Apr. 5, 1994

[54] LIQUID ABSORPTION AGENT

[75] Inventors: Toshiyuki Aizawa; Hitoshi Nakamura, both of Oita; Yoshikazu Hosoda, Kawasaki, all of Japan

[73] Assignee: Showa Denko K.K., Tokyo, Japan

[ * ] Notice: The portion of the term of this patent subsequent to Jan. 18, 2011 has been disclaimed.

[21] Appl. No.: 31,022

[22] Filed: Mar. 11, 1993

Related U.S. Application Data

[63] Continuation of Ser. No. 701,911, May 17, 1991, abandoned.

[30] Foreign Application Priority Data

Sep. 3, 1990 [JP] Japan ................. 2-230550

[51] Int. Cl.$^5$ ............... C08F 236/02; C08F 236/02; C08F 226/02
[52] U.S. Cl. .................. 526/307.6; 526/240; 526/264; 526/287; 526/303.1; 526/306; 526/307.1; 526/307.2; 526/312; 526/317.1; 526/318; 526/318.1; 526/342; 526/347; 526/333
[58] Field of Search .............. 526/307.6, 240, 306, 526/307.1, 303.1, 312

[56] References Cited

U.S. PATENT DOCUMENTS

| | | | |
|---|---|---|---|
| 4,500,437 | 2/1985 | Engelhardt | 252/8.55 |
| 4,522,997 | 6/1985 | Schmitz | 526/264 |
| 4,873,299 | 10/1989 | Nowakowsky | 526/73 |
| 5,126,395 | 6/1992 | End | 524/801 |

FOREIGN PATENT DOCUMENTS

| | | | |
|---|---|---|---|
| 0068159 | 5/1982 | European Pat. Off. | C08F 220/56 |
| 0105529 | 10/1983 | European Pat. Off. | C08F 226/02 |
| 0214454 | 8/1986 | European Pat. Off. | C08F 220/56 |
| 58-05305 | 1/1983 | Japan | C08F 8/12 |
| 59-22939 | 2/1984 | Japan | C08K 5/34 |
| 60-40108 | 3/1985 | Japan | C08F 30/02 |
| 60-42403 | 3/1985 | Japan | C08F 8/40 |
| 61-51007 | 3/1986 | Japan | C08F 8/12 |
| 61-53312 | 3/1986 | Japan | C08F 220/56 |

Primary Examiner—Fred Zitomer
Attorney, Agent, or Firm—Sughrue, Mion, Zinn, Macpeak & Seas

[57] ABSTRACT

A liquid absorption agent for water or organic solvents comprising, as a main component, a crosslinked N-vinylcarboxylic acid amide resin comprising the backbone chain of a homopolymer or copolymer comprising repeating units of the formula shown below crosslinked with a crosslinking agent:

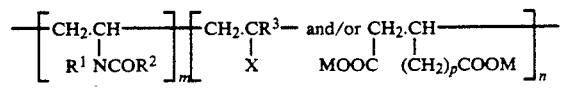

wherein $R^1$, $R^2$, and $R^3$ independently represent a hydrogen atom or methyl;

X represents a group —COOY, wherein Y represents a hydrogen atom, an alkali metal, $C_1$-$C_6$ alkyl, or lower alkyl substituted with hydroxyl, dialkylamino or quaternary ammonium group; a group —CONHZ, wherein Z represents a hydrogen atom or lower alkyl substituted with a dialkylamino group, quaternary ammonium group, sulfonic acid or an alkali metal salt thereof; cyano, 2-ketopyrrolidinyl, lower alkoxy, lower acyl, lower acyloxy or lower alkyl substituted with sulfonic acid or an alkali metal salt thereof, with a proviso that when $R^3$ is methyl, X is not cyano, 2-ketopyrrolidinyl, lower alkoxy, lower alkylcarbonyl, lower alkoxycarbonyl and lower alkyl substituted with sulfonic acid or a salt thereof;

M represents a hydrogen atom or an alkali metal;

p represents 0 or 1; and a molar ratio of m:n is 50–100:50–0.

8 Claims, No Drawings

LIQUID ABSORPTION AGENT

This is a continuation of application Ser. No. 07/701,911 filed May 17, 1991 now abandoned.

BACKGROUND OF THE INVENTION

1. Field of the Invention

The present invention relates to a liquid absorption agent for water or organic solvents comprising, as a main component, a crosslinked N-vinyl-carboxylic acid amide resin comprising the backbone (or main) chain of a homopolymer or copolymer containing at least 50 mole % of an N-vinylcarboxylic acid amide component crosslinked with a crosslinking agent. More specifically, the present invention relates to a liquid absorption agent having the following characteristics i.e., it is chemically stable, has an excellent absorption for water and organic solvents such as alcohol, particularly a good absorption for a liquid in which metal ions and organic ions co-exist in the system, and its absorbability is little influenced by the co-existing ions. Also, as a result of the absorption of a liquid, it is itself swelled or gelled to non-fluidize and solidify the co-existing liquid system, and exhibits a slow releasability and adhesion, thus having wide applications in various fields by making use of the excellent characteristics and functions of the crosslinked N-vinylcarboxylic acid amide resin.

2. Description of the Related Art

Liquid absorptive resins are used widely in such fields as medicine, sanitation, food industry, agriculture, horticulture, and civil engineering, and in all cases, there is a demand for a high swelling ratio and gel strength. Examples of water absorptive resins known in the art include hydrolyzates of starch-acrylonitril graft copolymers, neutralized products of starch-acrylic acid graft copolymers, saponified products of vinyl acetate-acrylate copolymers, hydrolyzates of acrylonitrile or acrylamide type crosslinked copolymers, and polyacrylic acid salt type crosslinked polymers or the like. These absorptive resins, however, are all polymeric electrolyte type crosslinked polymers, and therefore, although they exhibit an excellent swelling ability for water not containing any electrolyte, they exhibit a remarkably low swelling ability for an aqueous liquid containing a large amount of electrolytes such as blood, urine, aqueous fertilizer, and cement slurry. This is considered to be because a dissociation of the polymeric electrolyte, which is the backbone chain of the crosslinked polymer, is suppressed, and thus the expansion of the chain is reduced. Further, when polyvalent metal ions exist, a further ion crosslinking occurs by the carboxylic acid moiety in the backbone chain carboxylic acid to form a crosslinked polymer with a substantially higher crosslinking density than is necessary, which also causes a lowering of the swelling ratio. To avoid such drawbacks, for example, Japanese Unexamined Patent Publication (Kokai) No. 61-97312 discloses a method of preparing a water absorptive resin containing carboxyl groups in the chain structural units, in which an acrylic acid type compound is graft polymerized onto hydroxyethylcellulose, followed by hydrolysis. This method obtains an ion-resistant water absorptive resin by introducing nonionic polymers into a polymeric electrolyte backbone chain, but is not always satisfactory with respect to chemical stability of the backbone chain or the simplicity of the preparation method. Japanese Unexamined Patent Publication (Kokai) No. 60-55011 discloses a method of preparing an absorptive resin having an improved absorption ability for an aqueous electrolyte such as an aqueous sodium chloride, by a copolymerization of three kinds of compounds of (meth)acrylamide type compound, (meth)acrylic acid type compound and (meth)acrylic compound having a sulfonic group, in the presence of a divinyl type compound Japanese Unexamined Patent Publication (Kokai) No. 58-5305 discloses a water-swellable crosslinked polymer containing an N-vinyl compound, but since each polymer is intended to avoid an inhibition of a spreading of the backbone chain in an electrolyte solution by an introduction of relatively strong ionic dissociation groups, (meth)acrylamide or an N-vinyl compound is not substantially the main component, and thus a water absorptive resin with a high ion resistance cannot be always obtained. Further, as described above, because the backbone chain is a polymeric electrolyte, a large amount of electrolytes must be contained in the swelled gel, and accordingly, the gel does not always exhibit a sufficient effect as a water supplementing material for agricultural and horticultural use, and there is a demand for a material exhibiting a high function in this field. Similarly, these water supplementing materials also must have an excellent light resistance, due to the uses thereof, but a satisfactory solution has not been obtained also in this respect.

The water absorptive resins, as is obvious, form gelled products by an absorption of water, but exhibit no swellability with organic solvents such as alcohol, and the use thereof has been limited to, for example, water absorption and water retention.

SUMMARY OF THE INVENTION

Accordingly, the objects of the present invention are to eliminate the drawbacks possessed by water absorptive resins known in the art, as represented by crosslinked sodium polyacrylate, particularly the drawback of a remarkable lowering of the absorption ability for a liquid in which inorganic and organic ions such as metal salts, amines, carboxylic acids co-exist (i.e., electrolyte solution), or the drawback of a poor chemical stability in a natural high molecular compound or a chemically modified product thereof, and to provide a liquid absorption agent also having an absorption ability not only for an aqueous system but also other organic solvents such as alcohols, having a good adhesion of the gel formed by an absorption of the liquid, and having excellent re-utilizability of the water in the gel by plants.

Other objects and advantages of the present invention will be apparent from the following description.

In accordance with the present invention, there is provided a liquid absorption agent for water or organic solvents comprising, as the main component, a crosslinked N-vinyl-carboxylic acid amide resin comprising the backbone chain of a homopolymer or copolymer comprising at least 50 mole % or more of an N-vinylcarboxylic acid amide component crosslinked with a crosslinking agent, more particularly a crosslinked N-vinyl-carboxylic acid amide resin comprising a backbone chain of polymer comprising repeating units of the formula shown below crosslinked with a crosslinking agent:

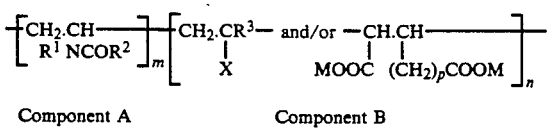

Component A        Component B wherein $R^1$, $R^2$, $R^3$ each represent a hydrogen atom or methyl group; X represents a group —COOY (Y represents hydrogen atom, an alkali metal, a $C_1$-$C_6$ alkyl group or a lower alkyl (e.g., $C_1$-$C_6$ alkyl) group substituted with hydroxyl group, a dialkylamino group or quaternary ammonium group), a group —CONHZ (Z represents a hydrogen atom or a lower alkyl (e.g., $C_1$-$C_6$ alkyl) group substituted with a dialkylamino group, quaternary ammonium group, sulfonic acid or an alkali metal salt thereof), cyano group, 2-ketopyrrolidinyl group, a lower alkoxy (e.g., $C_1$-$C_4$ alkoxy) group, a lower acyl group (e.g., a $C_2$-$C_4$ acyl group), a lower acyloxy group (e.g., a $C_2$-$C_4$ acyloxy group) or a lower alkyl (e.g., $C_1$-$C_3$ alkyl) group substituted with sulfonic acid or an alkali metal salt thereof, with the proviso that when $R_3$ is a methyl group, X is not a cyano group, 2-ketopyrrolidinyl group, a lower alkoxy group, a lower acyl group, a lower acyloxy group or a lower alkyl group substituted with sulfonic acid or a salt thereof; M represents a hydrogen atom or an alkali metal; p represents 0 or 1; and the molar ratio of m:n is 50–100:50–0.

According to the present invention, there is provided a liquid absorption agent which has wide applications in various fields by making full use of the excellent characteristics and functions of a crosslinked resin comprising, as the main component, an N-vinylcarboxylic acid amide. The resin is chemically stable and has a high light resistance, an excellent absorption ability for water and organic solvents such as alcohol, particularly having a high water absorption (organic solvent absorption) ratio for the liquid in which inorganic and organic ions such as metal salts, amines, and carboxylic acids even co-exist. The resin which itself is swelled and gelled can non-fluidize and solidify the co-existing liquid system simultaneously with a slow releasability and adhesion.

DESCRIPTION OF THE PREFERRED EMBODIMENTS

The liquid absorption agent of the present invention has a basic and primary function of absorbing water and organic solvents, but the water or organic solvents absorbed in the resin will be released depending on the external environment, and since the absorption-retention-release is reversible, it also exhibits a control function for these liquids (for example, when an aqueous system is made the object, for water absorption (or dehydration), water retention, water supply, and water content control). Also, since the resin of the present invention is chemically stable and has an excellent light resistance, the function can be exhibited repeatedly many times and the water retained in the resin can be well re-utilized by plants, and the gel itself exerts no adverse influence on the germination, root generation, and growth. The resin in the liquid is swelled and gelled, and the system supplemented with the resin has a lower fluidity, and finally is non-fluidized and solidified. Therefore, the resin has a shaping property for the system to which it is added. The non-fluidized and solidified (shaped) system can assume many states, from a very soft state to a shaped product having some elasticity, and various functions can be exhibited corresponding to the respective states. For example, in a relatively softer state, the resin-containing liquid adheres to an objective material, exhibiting a sealability or stickness, and a shape having elasticity exhibits a sound absorbing property by absorbing vibration or shock, in addition to water retention and water supply properties. Further, properties such as a slow releasability of the component retained in the gel, electroconductivity and high specific heat (heat accumulability, coldness retention, heat retention) of the gel-containing water also can be utilized. The function of absorption-retention-(slow) release and non-fluidization of a liquid organic compound are remarkable characteristics of the absorbent of the present invention, together with the ion resistance mentioned above, not found in the absorbent of the prior art.

Various functions such as absorption, release, control and releasability of liquid, and lowering of fluidity, solidification, shaping property, or adhesion, and coverage are causes and results, i.e., a series of phenomena intimately related to one another when viewed from various standpoints, and the basic function thereof is an absorption-gelling of liquid. Therefore, the term liquid absorption agent as used in the present invention should not be interpreted in the narrow sense of merely being an absorbent of liquid, but also should be seen to means various functions, actions and phenomena brought about as the result of (or accompanied by) a use of the crosslinked N-vinylcarboxylic acid amide resin as described above.

Such various functions (basically absorbency for water and organic solvents) can be obtained by the use of a crosslinked type N-vinylcarboxylic acid amide resin comprising the backbone chains of a homo- or co-polymer containing at least 50 mole % of an N-vinylcarboxylic acid amide component crosslinked with a crosslinking agent, and typical specific examples of the respective monomers of the component A (N-vinylcarboxylic acid amide component) and the component B (copolymer component) of the repeating units shown by the above formula may include those as set forth below.

Component A: N-vinylformamide, N-vinylacetamide, N-methyl-N-vinylformamide, N-methyl-N-vinylacetamide or the like, particularly preferably N-vinylacetamide.

Component B: acrylic acid, methacrylic acid (i.e., "(meth)acrylic acid") or alkali metal salts thereof such as sodium salts, potassium salts, etc.; alkylesters such as methyl esters, ethyl esters, propyl esters, butyl esters, pentyl esters, hexyl esters; hydroxy lower alkyl esters such as hydroxyethyl esters, hydroxypropyl esters, hydroxybutyl esters or the like; lower alkyl esters substituted with lower alkylamino group such as dimethylaminomethyl esters, dimethylaminoethyl esters, dimethylaminopropyl esters, dimethylaminobutyl esters, diethylaminomethyl esters, diethylaminoethyl esters, diethylaminopropyl esters, diethylaminobutyl esters or the like; lower alkyl esters substituted with quaternary ammonium group such as trimethylammonioethyl ester halides, trimethylammoniopropyl ester halides, triethylammonioethyl ester halides, triethylammoniopropyl ester halides or the like; amides; alkyl amides (preferably N-lower alkyl substituted amides) substituted with lower alkylamino groups such as dimethylaminomethylamides, dimethylaminoethylamides, dimethylaminopropylamides, dimethylaminobutylamides, diethylaminomethylamides, diethylaminoethylamides, diethylaminopropylamides, diethylaminobutylamides or the like; lower alkylamides substituted with quaternary ammonium group such as trimethylammonioethylamide halides, trimethylammoniopropylamide halides, triethylammonioethylamide halides, triethylammoniopropylamide halides or the like; lower alkylamides substituted with sulfonic acid or alkali metal sulfonate such as sulfomethylamides, sulfoethylamides, sulfopropylamides, sulfobutylamides, sodium sulfomethylamides, sodium sulfoethylamides, sodium sulfopropylamides, sodium sulfobutylamides, potassium sulfomethylamides, potassium sulfoethylamides, potassium sulfopropylamides, potassium sulfobutylamides or the like; acrylonitrile; N-vinyl-2-pyrrolidone; vinyl ethers such as methyl vinyl ether, ethyl vinyl ether, propyl vinyl ether, butyl vinyl ether or the like; vinyl ketones such as methyl vinyl ketone, ethyl vinyl ketone or the like; vinyl lower carboxylates such as vinyl acetate, vinyl propionate or the like; allylsulfonic acid or alkali metal salts thereof such as allylsulfonic acid, sodium allylsulfonate, potassium allylsulfonate or the like; maleic acid, sodium maleate potassium maleate, fumaric acid, sodium fumarate, itaconic acid, sodium itaconate, potassium itaconate and so on.

Among them, particularly (meth)acrylic acid, sodium (meth)acrylate, methyl (meth)acrylate, ethyl (meth)acrylate, propyl (meth)acrylate, butyl (meth)acrylate, hydroxyethyl (meth)acrylate, hydroxypropyl (meth)acrylate, hydroxybutyl (meth)acrylate, dimethylaminoethyl (meth)acrylate, trimethylammonioethyl (meth)acrylatechloride, acrylamide, sulfopropylacrylamide, sulfobutyl acrylamide, sodium sulfopropyl acrylamide, sodium sulfobutylacrylamide, acrylonitrile, methyl vinyl ether, ethyl vinyl ether, methyl vinyl ketone, ethyl vinyl ketone, vinyl acetate, sodium allylsulfonate, N-vinyl-2-pyrrolidone, maleic acid, sodium maleate, itaconic acid, sodium itaconate, etc. are preferable.

In the case of a copolymer, at least 50 mole % or more of the component A must be contained, as mentioned above, and at a ratio lower than this, the ion resistance, absorbability of organic compounds and light resistance, which are characteristics of the absorbent of the present invention, cannot be fully exhibited. A preferable range of the copolymer composition depends on the kind of the liquid to be absorbed, particularly the kind of co-existing solute and the concentration, etc., and cannot be generally specified.

For the crosslinking agent, a compound having at least two polymerizable unsaturated groups in one molecule can be used, and representative examples thereof include those set forth below: N,N'-lower alkylenebisacrylamides such as N,N'-methylenebisacrylamide, N,N'-1,2-ethylenebisacrylamide or the like; N,N'-α,ω-lower alkylenebis(N-vinylcarboxylic acid amide) such as N,N'-methylenebis(N-vinylacetamide), N,N'-1,3-propylenebis(N-vinylacetamide), N,N'-1,4-butylenebis(N-vinylacetamide), N,N'-1,5-pentylenebis(N-vinylacetamide), N,N'-1,6-hexylenebis(N-vinylacetamide), N,N'-1,7-heptylenebis(N-vinylacetamide), N,N'-1,8-octylenebis(N-vinylacetamide), N,N'-1,9-nonylenebis(N-vinylacetamide), N,N'-1,10-decylenebis(N-vinylacetamide), N,N'-diacetyl-N,N'-divinyl-1,3-butanediamine, N,N'-diacetyl-N,N'-divinyl-2,5-hexanediamine, N,N'-diacetyl-N,N'-divinyl-2,4-pentanediamine, N,N'-diacetyl-N,N'-divinyl-2,2-diethyl-1,3-propanediamine, N,N'-diacetyl-N,N'-divinyl-2,5-dimethyl-2,5-hexanediamine, N,N'-diacetyl-N,N'-divinyl-2,4-dimethyl-2,4-pentanediamine, N,N'-diacetyl-N,N'-divinyl-2,2-dimethyl-1,3-propanediamine, N,N'-diacetyl-N,N'-divinyl-2-ethyl-1,5-hexanediamine, N,N'-diacetyl-N,N'-divinyl-2-ethyl-2-methyl-1,3-propanediamine, N,N'-diacetyl-N,N'-divinyl-2-methyl-1,3-butanediamine, N,N'-diacetyl-N,N'-divinyl-2-methyl-1,5-pentanediamine, N,N'-1,3-propylenebis(N-vinylformamide), N,N'-1,4-butylenebis(N-vinylformamide), N,N'-1,5-pentylenebis(N-vinylformamide), N,N'-1,6-hexylenebis(N-vinylformamide), N,N'-1,7-heptylenebis(N-vinyl-formamide), N,N'-1,8-octylenebis(N-vinylformamide), N,N'-1,9-nonylenebis(N-vinyl-formamide), N,N'-1,10-decylenebis(N-vinylformamide), N,N'-diformyl-N,N'-divinyl-1,3-butanediamine, N,N'-diformyl-N,N'-divinyl-2,5-hexanediamine, N,N'-diformyl-N,N'-divinyl-2,4-pentanediamine, N,N'-diformyl-N,N'-divinyl-2,2-diethyl-1,3-propanediamine, N,N'-diformyl-N,N'-divinyl-2,5-dimethyl-2,5-hexanediamine, N,N'-diformyl-N,N'-divinyl-2,4-dimethyl-2,4-pentanediamine, N,N'-diformyl-N,N'-divinyl-2,2-dimethyl-1,3-propanediamine, N,N'-diformyl-N,N'-divinyl-2-ethyl-1,3-hexanediamine, N,N'-diformyl-N,N'-divinyl-2-ethyl-2-methyl-1,3-propanediamine, N,N'-diformyl-N,N'-divinyl-2-methyl-1,3-butanediamine, N,N'-diformyl-N,N'-divinyl-2-methyl-1,5-pentanediamine, N,N'-diacetyl-N,N'-divinyl-1,3-bis-aminomethylcyclohexane, N,N'-diacetyl-N,N'-divinyl-1,4-bis(aminomethyl)-cyclohexane, N,N'-diformyl-N,N'-divinyl-1,3-bis-(aminomethyl)cyclohexane, N,N'-diformyl-N,N'-divinyl-1,4-bis-(aminomethyl)cyclohexane or the like; N,N'-(diacetyl)-N,N'-(divinyl)-α,ω-diaminopolyethers such as N,N'-3-oxa-1,5-pentylene bis(N-vinylacetamide), N,N'-3,6-dioxa-1,8-octylene bis(N-vinylacetamide), N,N'-3,6,9-trioxa-1,11-undecylene bis(N-vinylacetamide), N,N'-3,6,9,12-tetraoxa-1,14-tetradecylene bis(N-vinylacetamide), N,N'-3-oxa-1,5-pentylene bis(N-vinylformamide), N,N'-3,6-dioxa-1,8-octylene bis(N-vinylformamide), N,N'-3,6,9-trioxa-1,11-undecylene bis(N-vinylformamide), N,N'-3,6,9,12-tetraoxa-1,14-tetradecylene bis(N-vinylformamide), N,N'-1,4-dimethyl-3-oxa-1,5-pentylene bis(N-vinylacetamide), N,N'-1,4,7-trimethyl-3,6-dioxa-1,8-octylene bis(N-vinylacetamide), N,N'-1,4,7,10-tetramethyl-3,6,9-trioxa-1,11-undecylene bis(N-vinylacetamide), N,N'-1,4,7,10,13-pentamethyl-3,6,9,12-tetraoxa-1,14-tetradecylene bis(N-vinyl-acetamide), N,N'-1,4-dimethyl-3-oxa-1,5-pentylene bis(N-vinylformamide), N,N'-1,4,7-trimethyl-3,6-dioxa-1,8-octylene bis(N-vinylformamide), N,N'-1,4,7,10-tetramethyl-3,6,9-trioxa-1,11-undecylene bis(N-vinylformamide), N,N'-1,4,7,10,13-pentamethyl-3,6,9,12-tetraoxa-1,14-tetradecylene bis(N-vinylformamide)or the like; xylylene bis(N-vinylcarboxylic acid amide) such as p-xylylene bis(N-vinyl-formamide), p-xylylene bis(N-vinylacetamide), m-xylylene bis(N-vinylform amide), m-xylylene bis(N-vinylacetamide) or the like; alkyleneglycol di(meth)acrylates such as ethylene glycol di(meth)acrylate, propylene glycol di(meth)acrylate, or the like; polyalkylene glycol di(meth)acrylates such as diethylene glycol di(meth)acrylate, triethylene glycol di(meth)acrylate, polyethylene glycol di(meth)acrylate, propylene glycol di(meth)acrylate, or the like; divinyl compounds such as divinyl benzene, divinyl ether, or the like; trifunctional group compounds such as trimethylolpropane tri(meth)acrylate, pentaerythritol tri(meth)acrylate, trimethylolpropane diallylether, pentaerythritol triallyl ether, triallyl phosphate, or the like; and so on.

Among them, particularly N,N'-methylenebisacrylamide, N,N'-1,4-butylenebis(N-vinylacetamide), N,N'-1,6-hexylenebis(N-vinylacetamide), N,N'-1,10-decylenebis(N-vinylacetamide), N,N'-3-oxa-1,5-pentylenebis(N-vinylacetamide), N,N'-3,6-dioxa-1,8-octylenebis(N-vinylacetamide), N,N'-p-xylylenebis(N-vinylacetamide), N,N'-diacetyl-N,N'-divinyl-1,4-bisaminomethylcyclohexane, may be included as preferable ones. The mixture of two or more compounds as mentioned above can also be used.

The amount of the crosslinking agent used is preferably from $2 \times 10^{-4}$ to 1 mole %, more preferably from $2.5 \times 10^{-4}$ to 0.2 mole %, most preferably from $5 \times 10^{-4}$ to $1 \times 10^{-2}$ mole %, based on the (co)polymerized component. In this connection, when the amount of the crosslinking agent used is more than 1 mole % based on the (co)polymerized component, the obtained resin has too high a crosslinking density, whereby its absorbing performance is remarkably lowered, but when it is smaller than $2 \times 10^{-4}$ mole %, the polymeric chains not crosslinked is increased, whereby it becomes readily soluble in water or organic solvents and a performance thereof as an absorbent cannot be expected.

The crosslinking reaction may be carried out by copolymerization of a polyfunctional monomer during polymerization, but this method is not limitative as it is also possible to effect a post-crosslinking. More specifically, straight chain polymers can be crosslinked by using crosslinking agents having reactive groups such as carboxylic acid or metal salt thereof, glycidyl, group, hydroxy groups, and amino groups, etc. For example, the object of the present invention also can be accomplished by allowing straight chain polymers copolymerized with sodium acrylate within the range shown in the present invention to react with the compounds having 2 or more glycidyl groups, for example, ethylene glycol diglycidyl ether within the above-mentioned specific range. Similarly, combinations of a glycidyl group and amine, carboxylic acid and a polyvalent metal cation, etc. are possible. In each case, the amount of crosslinking agent and the copolymer composition are important.

The polymerization process is not limited, but preferably is performed according to a method such as an aqueous solution polymerization, reverse phase suspension polymerization, or reverse phase emulsion polymerization.

For example, as the aqueous solution polymerization method, monomer components and crosslinking agents are uniformly dissolved in a solvent such as water, a hydrophilic organic solvent uniformly miscible with water, or a solvent mixture thereof, and after removal of dissolved oxygen in the system, by vacuum degassing or replacement with an inert gas such as nitrogen and, carbon dioxide, a polymerization initiator is added to carry out the reaction. The polymerization initiation temperature is generally about $-10°$ to $60°$ C., and the reaction time is about 1 to 10 hours.

The above-mentioned hydrophilic organic solvent includes lower alcohols such as methyl alcohol, ethyl alcohol, propyl alcohol or the like, cyclic ethers such as tetrahydrofuran, dioxane or the like, acetone, acetonitrile, N,N'-dimethylformamide, N,N'-dimethylacetamide, dimethyl sulfoxide, or the like. Among them, particularly, tetrahydrofuran, acetonitrile, N,N'-dimethyl formamide, N,N'-dimethyl acetamide, and dimethyl sulfoxide are preferred.

As the polymerization initiator, there may be employed peroxides, hydroperoxides, organic, inorganic peracids persulfates or salts thereof, azobis type compounds uniformly soluble in solvents, alone or redox type initiator by combination with a reducing agent, and representative examples thereof include those set forth below:

t-butylperoxide, t-amylperoxide, cumylperoxide, acetylperoxide, propionylperoxide, benzoylperoxide, benzoylisobutyrylperoxide, lauroyl peroxide, t-butyl hydroperoxide, cyclohexyl hydroperoxide, tetralin hydroperoxide, t-butyl peracetate, t-butyl perbenzoate, bis(2-ethylhexylperoxydicarbonate), 2,2-azobisisobutyronitrile, phenylazotriphenylethane, 2,2-azobis(2-amidinopropane)dihydrochloride, 2,2-azobis[2-(5-methyl-2-imidazoline-2-yl)propane]dihydrochloride, 2,2-azobis[2-(2-imidazoline-2-yl)propane]dihydrochloride, sodium persulfate, potassium persulfate, ammonium persulfate, hydrogen peroxide, combinations of persulfates with tertiary amines such as triethylamine, triethanolamine, and dimethylaniline, etc.

Among these, particularly, t-butyl peroxide, benzoyl peroxide, 2,2-azobis i-butyronitrile, 2,2-azobis(2-amidinopropane)dihydrochloride, 2,2-azobis[2-(5-methyl-2-imidazoline-2-yl)propane]dihydrochloride, 2,2-azobis[2-(2-imidazoline-2-yl)propane]dihydrochloride, sodium persulfate, potassium persulfate or ammonium persulfate, or a combination of persulfates and a tertiary amine such as triethylamine, triethanol amine or dimethylaniline are preferred.

The amount of the polymerization initiator used is preferably 0.0005 to 5 mole %, more preferably 0.001 to 1 mole %, most preferably 0.005 to 0.5 mole %, based on the (co)polymer component. In this connection, when the amount of the polymerization initiator used is more than 5 mole % based on the (co)polymerized component, the polymerization degree of the backbone polymer chain cannot be increased to thus increase the ratio of uncrosslinked polymer chains, whereby the polymer becomes readily soluble in water or organic solvents, and therefore cannot exhibit the performance expected as an absorbent. On the other hand, when it is smaller than 0.0005 mole %, the conversion of the polymerization reaction is not increased, and a drawback occurs in that the amount of residual monomer is increased.

The reaction product is a gel containing the solvent employed for the reaction, and is generally crushed by a rotatory system cutter, and further, the solvent is removed by a method such as heating or a reduced pressure, followed by drying, crushing and classification, to be made into a powder with a particle size of about $50\mu$ to 1 mm.

As the reverse phase suspension polymerization and reverse phase emulsion polymerization method, monomer components and a crosslinking agent are uniformly dissolved in water, and the solution is suspended or emulsified in an organic solvent immiscrible with water, to carry out the polymerization reaction. The polymerization initiator is not necessarily limited to water soluble products and those soluble in organic solvents also can be used. Accordingly, in addition to those mentioned above, for example, those set forth below also can be used.

Examples of the organic solvents include hydrocarbons such as hexane, cyclohexane, heptane, octane, benzene, toluene, xylene and ethylbenzene; halogenated hydrocarbons such as carbon tetrachloride and dichlorethane; mineral oils such as Isopar, etc.

In the reverse phase emulsion polymerization method, a surfactant is used as the dispersing agent, optionally together with a protective colloid. Examples of such a surfactant include sorbitane monostearate, sorbitane monopalmitate, polyvinyl alcohol, methyl cellulose, ethyl cellulose, hydroxymethyl cellulose, hydroxyethyl cellulose, carboxymethyl cellulose, carboxyethyl cellulose, etc.

Removal of the dissolved oxygen in the system and treatment of the reaction product, etc. are the same as described above, and the reaction conditions are not limited, but are generally as follows: amount of solvent employed; equal to 20-fold of the aqueous monomer solution, preferably equal to 10-fold, particularly equal to 5-fold, the amount of polymerization initiator employed; 0.0005 to 5 mole %, preferably 0.001 to 1 mole %, particularly 0.005 to 0.5 mole %, based on the monomer component and a polymerization initiation temperature of about 10° to 90° C., and reaction time of about 1 to 10 hours.

The molecular structure of the thus obtained resin has a three-dimensional structure formed by crosslinking of straight chain polymers comprising a homopolymer of an N-vinylcarboxylic acid amide or a copolymer thereof with another copolymer component. Primarily, the molecular weight of the backbone chain and the crosslinking density, will exert a strong control of the function as the liquid absorption agent of the present invention. For example, although theoretically it is possible to make the liquid absorption ability greater by making the backbone chain as large as possible and the crosslinking density as small as possible, the liquid absorption ability itself is limited, and if the distance between crosslinks becomes larger, the physical strength of the gel formed by an absorption of liquid is remarkably lowered, and further, the number of molecules not participating in the crosslinking is increased, to give a higher solubility. Therefore, it is important that the polymerization degree of the backbone chain is from 500,000 to 100, preferably 400,000 to 1000, particularly from 200,000 to 10,000, and that the crosslinking density is from 1/500,000 to 1/100, preferably from 1/300,000 to 1/1000, particularly from 1/200,000 to 1/10,000.

Where the backbone chain is a copolymer, the structure depends on the difference in the reactivity of the copolymerized component. For example, when acrylamide or, maleic acid, or the like is employed as the copolymerized component, the copolymer will frequently become an alternate copolymer; although this also depends on the charged molar ratio in the reaction. When acrylic acid or the like is employed, the copolymer will frequently become a block copolymer, and in the case of vinyl acetate or the like, the copolymer will frequently become a random copolymer. Nevertheless, the difference in the structure of the copolymer depending on the difference in the reactivity of these copolymerized components is not essential in the liquid absorption agent of the present invention as a whole, although respective characteristic functions may be added for individual use examples.

The crosslinked N-vinylcarboxylic acid amide resin (liquid absorption agent) as described above is obtained primarily as powder with particle sizes of about 50μ to 1 mm, but where liquid is absorbed, it is shaped as beads or a dispersion, cream, and paste-like viscous material, etc., and also may be formed into a strand, film, sheet, plate, and various formed products, and further, can be combined with various bases (materials) to be used in various shapes and forms.

The liquid absorption agent comprising a crosslinked type N-vinylcarboxylic acid amide resin as the main component has a basic main function of an excellent absorption of water and organic solvents, accompanied by an ion resistance, chemical stability and light resistance as described above, but also exhibits an absorption, release and control function and a releasability for liquid, a lowering of a fluidity of a system to which it is added, and a solidification, shaping or adhesion, sealability or a stickiness, and coverage. In a formed product having elasticity, in addition to the above-mentioned water retention and water supply, a sound absorption by absorbing vibration and shock. Further, such properties as a slow releasability of the component retained in the gel, an electroconductivity of water, and high specific heat properties (heat accumulability, coldness retention, heat retention) also can be utilized.

The liquid absorption agent of the present invention is contrasted to sodium polyacrylate crosslinked, well known water absorptive polymer in the art, which absorption performance is remarkably impaired when inorganic and organic ions such as metal salts, amines, and carboxylic acids co-exist in the liquid to be absorbed. On the other hand, the present absorption agent is little affected by a co-existence of ions, and therefore, the absorption is not substantially lowered even in an aqueous solution containing salts. The water absorbed and retained in the resin can be also re-utilized by plants, and the resin exerts no adverse influence on the germination, root generation, and growth thereof. The applications utilizing such characteristics, for example, include water retention (supply) agents for the soils in agricultural field, mountains and forests, particularly for such soils containing relatively more salt components, as a desert, artificial culture soil containing inorganic salts and fertilizers for tissue culture and artificial cultivation; absorbents of body fluids with a high salt content (urine, menses) for sanitary articles (diaper, napkin, tampon), etc.; absorbent of water containing a high calcium content for concrete curing and cement modifying; a non-fluidizing agent for deliquescent liquid is a calcium chloride type humectant; and dispersing agent for a metal salt solution for the preparation of ultra-fine particulate ceramics (complex forming agent with metal compound), etc.

Furthermore, the liquid absorbent agent according to the present invention is capable of absorbing water, various organic solvents and mixtures thereof, although crosslinked sodium polyacrylate products, which are typical conventional absorbents, are limited to be able to absorb water or a mixture of water and a part of lower alcohols. The typical examples of organic solvents to be absorbable by the present absorbents are those set forth below, which are generally called solvents having relatively high polarity:

Alcohols such as methanol, ethanol, 1-propanol, 1-bulanol, 2-butanol, isobutyl alcohol, isoamyl alcohol, cyclopentanol, allyl alcohol, 1,1,1,3,3,3-hexafluoro-2-propanol, 2-methoxyethanol, 2-ethoxyethanol, 2-buthoxy ethanol, 2-amino ethanol, ethylene glycol, trimethylene glycol, propylene glycol, 1,4-butanediol, 1,3-butanediol, 2,3-butanediol, triethylene glycol, and glycerol; phenols such as phenol, cresol; formamide, acetic acid, 2-pyrolidinene, dimethyl sulfoxide, pyridine; and the like. Furthermore, Organic solvents, which are not or little absorbable alone absorbable as mixing with other absorbable solvents, Typical examples of mixed absorbable solvents are those set forth below; mixtures of water and organic solvents such as water and N,N-dimethylformamide, phenol, acetone, tetrahydrofuran or dioxane; mixtures of organic solvent such as ethanol-acetone, ethanol-chloroform, ethanol-benzene, ethanol-ethyl acetate, methanol-methylene chloride, ethyl acetate-acetic acid.

It is not necessarily clear why the liquid absorbent agent according to the present invention can absorb a wide variety of solvents. It could be assumably due to the strong interaction between the crosslinked N-vinyl-carboxylic acid amide resin. Particularly the polarity of the solvents.

As a measure representing the polarity of solvent, a dielectric constant ($\epsilon$), a solubility parameter ($\delta$) and a solvent polarity parameter ($E_T$ value or Z value) are generally known. Among these parameters, it has been found as extensive studies that solvents having an $E_T$ value of 45 or more and mixed solvents having an $E_T$ value of 43 or more as a mixture can be appropriately absorbed by the present liquid absorbing agent. Those having an $E_T$ value smaller than the above-mentioned $E_T$ values are not substantially absorbed. Accordingly, as organic solvents to be absorbable by the present liquid absorbing agent are those having an $E_T$ value of 45 or more, as a single component and having an $E_T$ value of 43 or more, as a purulal components. Furthermore, in solvents having an $E_T$ value of 50 or more, preferably 53 or more, there are good correlationship between the $E_T$ value and the absorbability, in the case of either single solvents or mixed solvents.

Specific examples of representative applications other than those mentioned above include those set forth below. Of course, these are merely exemplary, and the uses of the liquid absorption agent of the present invention are not limited only to those mentioned below, and it can be widely utilized in various fields and, articles by utilizing the functions described above.

Articles for foods (articles for freshness retention, agents for dehydration, water retention, water supply, water content control); articles for agriculture and horticulture (soil improver, seedling growth or cultivation base material, water retention (supply) agent for vegetation (tree planting, afforestation of deserts, etc.), seed preparation, preventive agent (material) against freezing and frosting damages or dew formation); moisture, dew formation, droplet preventive agent for domestic and construction use; dehydration, water retention, water supply, water content control agent such as waterproof and waterstopping agent (material) for instruments, transmission cables, etc.; various slow release preparation in oral, perrectal pharmaceuticals, health foods, fodder additives, agricultural medicines, fertilizers, etc.; various medical articles (plastering agent, mucosa preparation, suppository); various agents for preparation (binder, coating agent); sealants, putty, paint aid, tacky tape for civil engineering, construction and domestic uses, various industries, salt damage and sand dust preventive agent (material); and other adhesion, coating bases or aids; waterstopping agents for civil engineering, excavating aid, lubricant for sandbags, pore shield, mines, tunnels, buildings, bridge piers, etc.; aromatics, deodorants, fire extinguishing agent, heat accumulating agent (coldness retention, heat retention); battery, electrode, sensor member; electrical parts, electroconductive improving agent (material) such as antistatic agent (material), etc.; thermal insulation (convection) preventive, vibration absorption, sound absorption material, packing; cosmetics (scrubbing face washing material, pack agent); agents for lowering a fluidity and, solidification, or shape forming in a contact lens detergent, etc.

The specific methods and amounts used of the liquid absorption agent of the present invention depend on the respective uses, and therefore, cannot be generally defined, but as a general rule, will not differ from the general, standard specifications and embodiments in the respective uses. However, due to its excellent functions and effects, use examples not found in the prior art can be expected, and the amount used can be reduced for accomplishing the same extent of an effect, as a matter of course.

EXAMPLES

The present invention will now be further illustrated by, but is by no means limited to, the following Examples.

EXAMPLE 1

To a glass reaction vessel, 750 g of water was added, then 200 g (2.4 mole) of N-vinylacetamide and 32 mg of N,N'-1,4-butylenebis(N-vinylacetamide) as a crosslinking agent were added to the vessel and dissolved in the water, the oxygen dissolved in the resulting solution was removed in advance by purging with nitrogen gas and thereafter a solution of 0.4 g of 2,2'-azobis(2-amidinopropane) dihydrochloride as a polymerization initiator in 49.6 g of water was added and the reaction was performed for 16 hours in a thermostatic water bath maintained at 30° C., in a nitrogen gas stream. The resulting gel-like reaction product was finely ground, then dehydrated with acetone, and dried at 105° C. for 5 hours. The dried product was finely pulverized and classified into a product of 48 to 100 mesh. The resulting resin had an average degree of polymerization of 20,000 and a crosslinking density of 1/16000.

EXAMPLE 2

The same procedures used in Example 1 were repeated except that N-vinylformamide, in the same amount, was substituted for the N-vinylacetamide to give a resin. The resulting resin had an average degree of polymerization of 19,000 and a crosslinking density of 1/19000.

EXAMPLE 3

The same procedures used in Example 1 were repeated except that N-methyl-N-vinylformamide, in the same amount, was substituted for the N-vinylacetamide to give a resin. The resulting resin had an average degree of polymerization of 19,000 and a crosslinking density of 1/16000.

EXAMPLE 4

The same procedures used in Example 1 were repeated except that N-methyl-N-vinylacetamide, in the same amount, was substituted for the N-vinylacetamide to give a resin. The resulting resin had an average degree of polymerization of 15,000 and a crosslinking density of 1/14000.

EXAMPLE 5

The same procedures used in Example 1 were repeated except that a mixture of 160 g (1.88 mole) of N-vinylacetamide and 40 g (0.43 mole) of sodium acrylate was substituted for 200 g of the N-vinylacetamide used in Example 1 to give a resin. The resulting resin had an average degree of polymerization of 22,000 and a crosslinking density of 1/16000.

EXAMPLES 6 TO 28

The same procedures used in Example 5 were repeated except that a variety of copolymerizable monomer components, in the same amount, were substituted for the sodium acrylate as the copolymerizable monomer component to give the corresponding resins. The amounts and kinds of the monomer components as well as the average degree of polymerization and the crosslinking density of the resulting resins are summarized in the following Table 1-1.

TABLE 1-1

| | Copolymerizable Components | | |
|---|---|---|---|
| | | Crosslinked Polymer | |
| Polymer No. | $B_m$ (mole) | Av. Deg. of Polymerization | Crosslinking Density |
| 6 | $B_1$ 0.37 | 21,000 | 1/15000 |
| 7 | $B_2$ 0.52 | 19,000 | 1/16000 |
| 8 | $B_3$ 0.35 | 17,000 | 1/15000 |
| 9 | $B_4$ 0.31 | 18,000 | 1/15000 |
| 10 | $B_5$ 0.28 | 15,000 | 1/15000 |
| 11 | $B_6$ 0.37 | 20,000 | 1/15000 |
| 12 | $B_7$ 0.35 | 18,000 | 1/15000 |
| 13 | $B_8$ 0.35 | 18,000 | 1/15000 |
| 14 | $B_9$ 0.32 | 17,000 | 1/15000 |
| 15 | $B_{10}$ 0.56 | 20,000 | 1/16000 |
| 16 | $B_{11}$ 0.56 | 19,000 | 1/16000 |
| 17 | $B_{12}$ 0.19 | 18,000 | 1/14000 |
| 18 | $B_{13}$ 0.18 | 19,000 | 1/14000 |
| 19 | $B_{14}$ 0.75 | 22,000 | 1/18000 |
| 20 | $B_{15}$ 0.56 | 20,000 | 1/16000 |
| 21 | $B_{16}$ 0.52 | 20,000 | 1/16000 |
| 22 | $B_{17}$ 0.52 | 21,000 | 1/16000 |
| 23 | $B_{18}$ 0.69 | 25,000 | 1/17000 |
| 24 | $B_{19}$ 0.56 | 20,000 | 1/16000 |
| 25 | $B_{20}$ 0.28 | 14,000 | 1/15000 |
| 26 | $B_{21}$ 0.36 | 18,000 | 1/15000 |
| 27 | $B_{22}$ 0.25 | 14,000 | 1/14000 |
| 28 | $B_{23}$ 0.25 | 14,000 | 1/14000 |

Remarks $B_1$: sodium methacrylate; $B_2$: methyl acrylate; $B_3$: ethyl acrylate; $B_4$: butyl acrylate; $B_5$: butyl methacrylate; $B_6$: hydroxyethyl acrylate; $B_7$: hydroxyethyl methacrylate; $B_8$: hydroxypropyl acrylate; $B_9$: hydroxypropyl methacrylate; $B_{10}$: acrylamide; $B_{11}$: dimethylaminoethyl methacrylate; $B_{12}$: dimethylaminoethyl methacrylate methylchloride quaternary salt; $B_{13}$: sodium 2-acrylamido-2-methylpropanesulfonate; $B_4$: acrylonitrile; $B_{15}$: methyl vinyl ketone; $B_{16}$: ethyl vinyl ketone; $B_{17}$: vinyl acetate; $B_{18}$: methyl vinyl ether; $B_{19}$: ethyl vinyl ether; $B_{20}$: sodium allylsulfonate; $B_{21}$: N-vinyl-2-pyrrolidone; $B_{22}$: sodium maleate; $B_{23}$: sodium itaconate.

EXAMPLE 29

The same procedures used in Example 5 were repeated except that 1 g of N,N'-methylenebisacrylamide was substituted for 32 mg of N,N'-1,4-butylenebis(N-vinylacetamide) as the crosslinking agent to give a resin. The resulting resin had an average degree of polymerization of 20,000 and a crosslinking density of 1/350.

EXAMPLE 30

The same procedures used in Example 5 were repeated except that N,N'-1,6-hexylenebis(N-vinylacetamide), in the same molar amount, was substituted for the N,N'-1,4-butylenebis(N-vinylacetamide) as the crosslinking agent to give a resin. The resulting resin had an average degree of polymerization of 18,000 and a crosslinking density of 1/16000.

EXAMPLES 31 TO 35

The same procedures used in Example 5 were repeated except that a variety of crosslinking agents, in the same molar amount, were substituted for the N,N'-1,4-butylenebis(N-vinylacetamide) as the crosslinking agent to give the corresponding resins. The amounts and kinds of the crosslinking agents as well as the average degree of polymerization and the crosslinking density of the resulting resins are summarized in the following Table 1-2.

TABLE 1-2

| | Kinds of Crosslinking Agents | | |
|---|---|---|---|
| | | Crosslinked Polymer | |
| | Crosslinking Agent | Av. Deg. of | Crosslinking |
| No. | Co (m mole) | Polymerization | Density |
| 31 | $C_1$ 0.144 | 18,000 | 1/16000 |
| 32 | $C_2$ 0.144 | 21,000 | 1/16000 |
| 33 | $C_3$ 0.144 | 19,000 | 1/16000 |
| 34 | $C_4$ 0.144 | 20,000 | 1/16000 |
| 35 | $C_5$ 0.144 | 18,000 | 1/16000 |

Remarks $C_1$: N,N'-1,10-decylenebis(N-vinylacetamide); $C_2$: N,N'-3-oxa-1,5-pentylenebis(N-vinylacetamide); $C_3$: N,N'-3,6-dioxa-1,8-octylenebis(N-vinylacetamide); $C_4$: N,N'-p-xylylenebis(N-vinylacetamide); $C_5$: N,N'-diacetyl-N,N'-divinyl-1,4-bis(aminomethyl)cyclohexane.

EXAMPLE 36

The same procedures used in Example 5 were repeated except that there were used a mixture of 150 g (1.76 mole) of N-vinylacetamide and 50 g (0.53 mole) of sodium acrylate as the monomer component, 31 mg of N,N'-1,4-butylenebis(N-vinylacetamide) as the crosslinking agent and 0.29 g of 2,2'-azobis(2-amidinopropane) dihydrochloride as the polymerization initiator to give a resin. The resulting resin had an average degree of polymerization of 21,000 and a crosslinking density of 1/16000.

EXAMPLE 37 TO 43

The same procedures used in Example 36 were repeated except that a variety of polymerization initiators were substituted for the 2,2'-azobis(2-amidinopropane) dihydrochloride to give corresponding resins. The amounts and kinds of the polymerization initiators used as well as the average degree of polymerization and the crosslinking density of the resulting resins are summarized in the following Table 1-3.

TABLE 1-3

| | Polymerization Initiator Components | | |
|---|---|---|---|
| | | Crosslinked Polymer | |
| Polymerization Initiator | | Av. Deg. of | Crosslinking |
| No. | $D_p$ (mole) | Polymerization | Density |
| 37 | $D_1$ 0.045 | 22,000 | 1/16000 |
| 38 | $D_2$ 0.077 | 19,000 | 1/16000 |
| 39 | $D_3$ 0.073 | 20,000 | 1/16000 |
| 40 | $D_4$ 0.513 | 20,000 | 1/16000 |
| 41 | $D_5$ 0.077 | 19,000 | 1/16000 |
| 42 | $D_6$ 0.077 | 20,000 | 1/16000 |
| 43 | $D_7$ 0.077 | 21,000 | 1/16000 |

Remarks $D_1$: potassium persulfate; $D_2$: ammonium persulfate; $D_3$: sodium persulfate; $D_4$: hydrogen peroxide/ferrous chloride; $D_5$: ammonium persulfate/triethanolamine; $D_6$: ammonium persulfate/sodium sulfite; $D_7$: ammonium persulfate/sodium thiosulfate.

EXAMPLE 44

The same procedures used in Example 36 were repeated except that the amount of the N,N'-1,4-butylenebis(N-vinylacetamide) was reduced to 24 mg and that 5 mg of N,N'-methylenebisacrylamide was added to give a resin. The resulting resin had an average degree of polymerization of 20,000 and a crosslinking density of 1/16000.

EXAMPLE 45

The same procedures used in Example 36 were repeated except that there were used 98 g (1.15 mole) of N-vinylacetamide and 107 g (1.14 mole) of sodium acrylate as monomers and that 15 mg of N,N'-1,4-butylenebis(N-vinylacetamide) and 11 mg of N,N'-methylenebisacrylamide were used as crosslinking agents to give a resin. The resulting resin had an average degree of polymerization of 21,000 and a crosslinking density of 1/16000.

EXAMPLE 46

To a glass reaction vessel, 250 g of water was added, then 98 g (1.15 mole) of N-vinylacetamide and 107 g (1.14 mole) of sodium acrylate, 11 mg of N,N'-methylenebisacrylamide and 15 mg of N,N'-1,4-butylenebis(N-vinylacetamide) as crosslinking agents were added to the vessel and dissolved in the water, then 1,000 g of n-hexane and 20 g of sorbitan monopalmitate were added thereto, the oxygen dissolved in the resulting solution was removed in advance by purging with nitrogen gas in a thermostatic water bath maintained at 30° C. with vigorous stirring of the solution, thereafter a solution of 0.4 g of 2,2'-azobis(2-amidinopropane) dihydrochloride as a polymerization initiator in 49.6 g of water was added and the reaction was continued for 16 hours in a nitrogen gas stream. The resulting particulate reaction product dispersed in the solvent was removed by filtration and dried at 105° C. for 5 hours. The dried product was classified into a product of 48 to 100 mesh. The resulting resin had an average degree of polymerization of 21,000 and a crosslinking density of 1/16000.

EXAMPLE 47

The same procedures used in Example 46 were repeated except that sorbitan monostealate, in the same amount, was substituted for the sorbitan monopalmitate as the surfactant to give a resin. The resulting resin had an average degree of polymerization of 21,000 and a crosslinking density of 1/16000.

EXAMPLE 48

The same procedures used in Example 46 were repeated except that only N-vinylacetamide was used as the monomer component in an amount of 205 g to give a resin. The resulting resin had an average degree of polymerization of 20,000 and a crosslinking density of 1/16000.

EXAMPLE 49

The same procedures used in Example 48 were repeated except that sorbitan monostearate, in the same amount, was substituted for the sorbitan monopalmitate as the surfactant to give a resin. The resulting resin had an average degree of polymerization of 20,000 and a crosslinking density of 1/16000.

COMPARATIVE EXAMPLE 1

The same procedures used in Example 1 were repeated except that 7 g of N,N'-1,4-butylenebis(N-vinylacetamide) was used as the crosslinking agent to give a comparative resin. The resulting resin X had an average degree of polymerization of 18,000 and a crosslinking density of 1/75.

COMPARATIVE EXAMPLE 2

The same procedures used in Example 1 were repeated except that 0.5 g of N,N'-butylenebis(N-vinylacetamide) was used as the crosslinking agent to give a comparative resin. The resulting resin Y had an average degree of polymerization of 18,000 and a crosslinking density of 1/1050000.

COMPARATIVE EXAMPLE 3

The same procedures used in Example 1 were repeated except that 50 g (0.59 mole) of N-vinylacetamide and 150 g (1.60 mole) of sodium acrylate were used as the monomer component to give a comparative resin. The resulting resin Z had an average degree of polymerization of 21,000 and a crosslinking density of 15000.

TEST EXAMPLE 1 (ABSORPTION OF AQUEOUS SOLUTION)

To 200 ml of a solution to be absorbed was gradually added 500 mg of an absorptive resin with stirring, the stirring was interrupted when the resin was sufficiently dispersed in the solution, the dispersion was allowed to stand for 2 hours, then the resin which had absorbed the solution and become swollen, to thus cause gelation, was filtered off through a 200 mesh sieve, and the weight of the resin remaining on the sieve was determined.

*Absorption Capacity* $=$ (wt. of gelled resin $-$ wt. of resin)/(wt. of resin)

Kinds of Solution to be Absorbed:
A: Aqueous solution of common salt (0.9% physiological saline)
B: Aqueous solution containing inorganic salts and organic substances (Corresponding to human urine) having the following composition: NaCl 0.79%; $K_2SO_4$ 0.20%; $MgSO_4$ 0.11%; $CaCl_2 \cdot 2H_2O$ 0.08%; urea 1.94%
C-a: Aqueous solution of calcium chloride (10%)
C-b: Aqueous solution of calcium chloride (saturated solution)
C-c: Aqueous solution of calcium hydroxide (saturated solution)

The results thus obtained are summarized in the following Table 2 and Table 3.

TEST EXAMPLE 2 (ABSORPTION OF ORGANIC SOLVENT)

To 50 ml of a solution to be absorbed was added 100 mg of an absorptive resin and the resin was visually observed to determine how the resin absorbed the solution, to cause a swelling and gelation thereof, while stirring the dispersion at room temperature at intervals.

Resins having a good absorptivity caused a gelation within 30 minutes to several hours, while those having an inferior absorptivity still remained in an approximately white powdery condition even after one week.

Sample Resin: Crosslinked N-vinylacetamide polymer (average degree of polymerization of the main chain: about 20,000; crosslinking agent: N,N'-1,4-butylenebis (N-vinylacetamide); crosslinking density: about 1/16,000).

The absorption ability was evaluated on the basis of the following criteria:

++: Gelation was observed within one day
—: No gelation was observed even after the lapse of one week The results obtained are listed in the following Table 4 together with an $E_T$ value of each solvent. No sample existed which caused gelation between one day to several days.

TABLE 2-1

| | Absorption of Aqueous Solution | |
|---|---|---|
| Test No. | Physiological Saline A (g/g) | Aqueous Solution B of Mixed Salts (g/g) |
| 1 | 77 | 70 |
| 2 | 76 | 69 |
| 3 | 71 | 65 |
| 4 | 73 | 66 |
| 5 | 96 | 87 |
| 6 | 95 | 86 |
| 7 | 72 | 66 |
| 8 | 70 | 64 |
| 9 | 69 | 63 |
| 10 | 68 | 62 |
| 11 | 73 | 67 |
| 12 | 73 | 66 |
| 13 | 70 | 66 |
| 14 | 69 | 65 |
| 15 | 68 | 69 |
| 16 | 73 | 65 |
| 17 | 78 | 71 |
| 18 | 100 | 91 |

TABLE 2-2

| | Absorption of Aqueous Solution | |
|---|---|---|
| Test No. | Physiological Saline A (g/g) | Aqueous Solution B of Mixed Salts (g/g) |
| 19 | 69 | 63 |
| 20 | 70 | 62 |
| 21 | 66 | 61 |
| 22 | 70 | 64 |
| 23 | 68 | 63 |
| 24 | 71 | 65 |
| 25 | 75 | 69 |
| 26 | 76 | 70 |
| 27 | 89 | 81 |
| 28 | 86 | 80 |
| 29 | 49 | 45 |
| 30 | 95 | 87 |
| 31 | 94 | 86 |
| 32 | 95 | 87 |

TABLE 2-3

| | Absorption of Aqueous Solution | |
|---|---|---|
| Test No. | Physiological Saline A (g/g) | Aqueous Solution B of Mixed Salts (g/g) |
| 33 | 96 | 88 |
| 34 | 95 | 86 |
| 35 | 94 | 89 |
| 36 | 97 | 88 |
| 37 | 85 | 78 |
| 38 | 85 | 77 |
| 39 | 86 | 79 |
| 40 | 89 | 81 |
| 41 | 98 | 90 |
| 42 | 91 | 83 |
| 43 | 90 | 82 |
| 44 | 100 | 92 |
| 45 | 108 | 95 |
| 46 | 106 | 98 |
| 47 | 100 | 91 |
| 48 | 82 | 73 |
| 49 | 80 | 70 |
| X | — | 3 |
| Y | — | dissolved and not determined |
| Z | — | 33 |

TABLE 3

| | Absorption of Aqueous Calcium Solution | | |
|---|---|---|---|
| Test No. | c - a | c - b | c - c |
| 1 | 73 (g/g) | 51 (g/g) | 29 (g/g) |
| 36 | 62 (g/g) | 34 (g/g) | 15 (g/g) |
| 46 | 48 (g/g) | 29 (g/g) | 1 (g/g) |
| X | 3 (g/g) | 3 (g/g) | — |
| Y | dissolved and not determined | dissolved and not determined | dissolved and not determined |
| Z | — | 5 (g/g) | 1 (g/g) |

The $E_T$ values of various solvents are shown in the following Table 4-1 (1)–(3) and 4-2 (1) and (2).

TABLE 4-1

| (1) (Single Solvent) | | |
|---|---|---|
| Solvent | Absorptivity | $E_T$ |
| HFIP | ++ | 65.3 |
| water | ++ | 63.1 |
| phenol | ++ | 61.4 |
| p-cresol | ++ | 60.8 |
| glycerol | ++ | 57.0 |
| formamide | ++ | 56.6 |
| glycol | ++ | 56.3 |
| methanol | ++ | 55.5 |
| trimethylene glycol | ++ | 54.9 |
| propylene glycol | ++ | 54.1 |
| 1,4-butanediol | ++ | 53.5 |
| triethylene glycol | ++ | 53.5 |
| 1,3-butanediol | ++ | 52.8 |
| 2-methoxyethanol | ++ | 52.3 |
| allyl alcohol | ++ | 52.1 |
| N-methylacetamide | — | 52.0 |
| ethanol | ++ | 51.9 |

HFIP: 1,1,1,3,3,3-hexafluoro-2-propanol

TABLE 4-1

| (2) (Single Solvent) | | |
|---|---|---|
| Solvent | Absorptivity | $E_T$ |
| 2-aminoethanol | ++ | 51.8 |
| 2,3-butanediol | ++ | 51.8 |
| acetic acid | ++ | 51.2 |
| 2-ethoxyethanol | ++ | 51.0 |
| 1-propanol | ++ | 50.7 |
| 1-butanol | — | 50.2 |
| 2-butoxyethanol | ++ | 50.2 |
| ethyl acetoacetate | — | 49.4 |
| amyl alcohol | — | 49.1 |
| isoamyl alcohol | ++ | 49.0 |
| 1-hexanol | — | 48.8 |
| isopropyl alcohol | — | 48.6 |
| isobutyl alcohol | ++ | 48.6 |
| 2-pyrrolidinone | ++ | 48.3 |
| 1-octanol | — | 48.3 |

TABLE 4-1-continued

| Solvent | (2) (Single Solvent) | |
|---|---|---|
| | Absorptivity | $E_T$ |
| 2-butanol | ++ | 47.1 |
| cyclopentanol | ++ | 47.0 |
| acetonitrile | − | 46.0 |

TABLE 4-1

| Solvent | (3) (Single Solvent) | |
|---|---|---|
| | Absorptivity | $E_T$ |
| DMSO | ++ | 45.0 |
| NMP | − | 44.1 |
| DMF | − | 43.8 |
| DMAc | − | 43.7 |
| acetone | − | 42.2 |
| nitrobenzene | − | 42.0 |
| methylene chloride | − | 41.1 |
| pyridine | − | 40.2 |
| chloroform | − | 39.1 |
| ethyl acetate | − | 38.1 |
| THF | − | 37.4 |
| chlorobenzene | − | 36.8 |
| 1,4-dioxane | − | 36.3 |
| diethylamine | − | 35.4 |
| benzene | − | 34.5 |
| triethylamine | − | 33.3 |
| cyclohexane | − | 32.1 |

THF: tetrahydrofuran; DMSO: dimethylsulfoxide; NMP: N-methyl-2-pyrrolidinone; DMF: N,N-dimethyl-formamide; DMAc: N,N-dimethylacetamide.

TABLE 4-2

| Solvent | (1) (Mixed Solvent) | | |
|---|---|---|---|
| | Solvent Composition (v/v) | Absorptivity | $E_T$ |
| water/dioxane | 0:100 | − | 36 |
| | 10:90 | − | 46 |
| | 30:70 | ++ | 51 |
| | 50:50 | ++ | 54 |
| | 100:0 | ++ | 63 |
| ethanol/acetone | 0:100 | − | 42 |
| | 10:90 | − | 47 |
| | 50:50 | ++ | 51 |
| | 100:0 | ++ | 52 |
| chloroform/ethanol | 0:100 | ++ | 52 |
| | 12:88 | ++ | 51 |
| | 50:50 | ++ | 48 |
| | 60:40 | ++ | 47 |
| | 70:30 | ++ | 46 |
| | 80:20 | ++ | 48 |
| | 90:10 | ++ | 44 |
| | 100:0 | − | 39 |

TABLE 4-2

| Solvent | (2) (Mixed Solvent) | | |
|---|---|---|---|
| | Solvent Composition (v/v) | Absorptivity | $E_T$ |
| methanol/methylene chloride | 0:100 | − | 41 |
| | 4:96 | − | 46 |
| | 9:91 | ++ | 48 |
| | 39:61 | ++ | 51 |
| | 100:0 | ++ | 56 |
| water/acetone | 0:100 | − | 42 |
| | 20:80 | − | 48 |
| | 40:60 | − | 51 |
| | 50:50 | − | 52 |
| | 60:40 | ++ | 53 |
| | 100:0 | ++ | 63 |
| water/THF | 0:100 | − | 37 |
| | 40:60 | − | 48 |
| | 80:20 | ++ | 51 |
| | 100:0 | ++ | 63 |

APPLICATION EXAMPLE 1

The water in the gel of the present invention is gradually released and can be reused by plants. In addition, the resin makes it possible to absorb and release (water supply) aqueous solutions of fertilizers having a practical concentration or water containing other inorganic or organic ion components besides pure water. Therefore, it is obvious that the resins can be used for fertilizing, soil improvement and as an artificial culture medium, and is convenient, in particular, for the transplantation of young seedlings and turf and tree planting in the mountains which has poor irrigation, or for erosion control and torrential improvement as well as afforestation of constructed land, or for water retention/water supply during an afforestation of a desert. In this connection, commercially available water absorptive resins of the prior art show an extremely low absorption of water containing ion components, and even when gelled with water containing no ions in advance, the utilizability of the water in the gel by plants is poor and sometimes chemical damage may be caused, and thus the utilization as described above is difficult.

This embodiment will be explained in more detail with reference to the following typical examples.

Sample Resins:

A) crosslinked N-vinylacetamide polymer (average degree of polymerization of the main chain: about 20,000; crosslinking agent: N,N'-1,4-butylenebis (N-vinylacetoamide); crosslinking density: about 1/16,000).

B) crosslinked N-vinylacetamide/sodium acrylate polymer (molar ratio of the monomers: 50/50; average degree of polymerization of the main chain: about 20,000; crosslinking agent: N,N'-1,4-butylenebis(N-vinylacetamide) and N,N'-methylenebisacrylamide; crosslinking density: about 1/17,000).

C) crosslinked sodium acrylate polymer (average degree of polymerization of the main chain: about 60,000; crosslinking agent: N,N'-methylenebisacrylamide; crosslinking density: about 1/10,000).

D) agar

Effect of Resin on Growth

1) To a group of shales (diameter = 10 cm) was added a gel prepared by adding 1% by weight each of the sample resins or agar to distilled water and uniformly mixing same, seeds of edible millet and lettuce were bedded therein respectively, and the gels were allowed to stand in a green house to determine the effect thereof on the germination, rooting and growth thereof.

No significant difference was observed in the germination, rooting and growth between the gel of sample resin A) and the agar gel used as a control. When the gel of the sample resin B) was used, the germination was slightly delayed, but the seedling grew without any particular problem. On the other hand, when the gel of the sample resin C) was used, the rooting and germination were markedly inhibited and the seedling was very undergrown.

2) To a group of pots (diameter = 15 cm) was added a predetermined amount of the sand uniformly mixed with 1% by weight each of the sample resins, seeds of wheat were seeded therein, followed by allowing to stand in a green house. Water was supplied every day. While thinning during culturing, when the standard grass height became about 10 cm after 5 weeks from the seeding, the final watering was effected and the water supply was stopped to observe the wilting conditions of the seedlings.

In the pots containing the sample resin A), the wilting started a 9 days after the stops of water supply and in the pots containing the sample resin B), the wilting started 7 days after the stop of water supply. On the other hand, in the pots containing the sample resin C), the wilting started 4 days after the stop of water supply and is the sand containing no resins, the wilting started 3 days after the stop of water supply.

3) To a group of pots (diameter=15 cm) was added a predetermined amount of the earthing up (mixed soil of volcanic ask soil/sand=1:1) uniformly mixed with 1% by weight each of the sample resins, young plants of cucumber (3 true leaves, grass height=15-20 cm) were transplanted. Water was supplied only once after transplanting and the transplanted plants were allowed to stand for 10 days without supplying water to observe the rooting condition of the young plants.

In the pots containing the sample resin A), all the transplanted young plants were rooted and in the pots containing the sample resin B), most of the trains planted young plants were rooted. However, in the pots containing no resins, most of the transplanted young plants were dead or nearly dead. Further, in the pots containing the sample resin C), nearly two third of the transplanted young plants were dead or nearly dead and the remaining young plants were wilted.

4) To a group of pots (diameter=15 cm) was added a predetermined amount of earthing up (mixed soil of volcanic ash soil/sand=1:1) uniformly mixed with 1% by weight each of the sample resins, a fertilizing liquid having the following composition was added.

$NH_4NO_3$ 58 ppm, $KNO_3$ 58 ppm, $NaNO_3$ 74 ppm, $KH_2PO_4$ 38 ppm, $MnSO_4 7H_2O$ 2 ppm, $CaCl_2.2H_2O$ 52 ppm, Fe.EDTA 18 ppm.

Thereafter, young plants of tomato (2 true leaves, grass height=10-15 cm) were transplanted to observe the effect on the rooting conditions and growth of the transplanted young plants.

No significant difference was observed in the conditions of rooting and growth between the pots containing the sample resin A) and the pots containing no resins, and the all the transplanted young plants exhibited prosperous growing conditions. In the pots containing the sample resins B), most of the transplanted young plants was rooted and exhibited prosperous growing conditions, whereas, in the pots containing the sample C), most of the transplanted young plants were dead or nearly dead with the lapse of two weeks.

APPLICATION EXAMPLE 2

If the resin of the present invention is brought into contact with an aqueous solution or a suspension containing a reactive component (such as metal ions and/or oxides), a gel comprising the aqueous solution or suspension is formed. The gel is dried and then calcined under heating to decompose and evaporate the resin component whereby the component (metal oxide) incorporated into the matrix of the crosslinked polymer is converted into fine particles having a particle size on the order of several nanometers. In this case, if the calcination under heating is performed in a non-oxidizing atmosphere, such fine particles are obtained in the form of a mixture with carbon particles derived from the resin component or a reaction product. Further, even a component such as aluminum chloride, which causes gasification upon heating, can be calcined under heating to convert it into fine particles. More specifically, an aqueous solution thereof is gelled, reacted with ammonium hydroxide in the gel to convert it into aluminum hydroxide and then calcined under heating. Moreover, although a part of the alumina sol or silica sol is suspended in water in the form of fine particles having a particle size of several nanometers, it can be incorporated into the matrix of a polymer in the form of a water absorptive gel like the soluble components such as metal ions. On the other hand, to obtain a ceramics article other than powder, a water-absorbed gel is formed into a predetermined shape and then calcined under heating. In this case, the resulting particles must be firmly coagulated, contrary to the case wherein fine powdery particles are formed. Therefore, the temperature during the calcination under heating must be optionally elevated and the time therefor must be extended.

In all cases, the possibility of realizing these techniques can be increased by the use of the resin of the present invention, which has an ability to form a gel through the absorption of an aqueous solution or a colloidal solution containing ions as such.

Representative examples thereof will be discussed below in detail.

Sample Resin: Crosslinked N-Vinylacetamide Polymer (average degree of polymerization of the main chain: about 20,000;

Crosslinking Agent: N,N'-1,4-butylenebis (N-vinylacetamide); crosslinking density: about 1/16,000)

1) 10 g of $Al(NO_3)_3.9H_2O$ was dissolved in 25 ml of water, 1 g of the sample resin was added thereto and uniformly mixed to give a gel as a whole, the gel was dried and then introduced into an alumina crucible. The temperature of the dried gel was elevated up to 1,000° C. over about 6 hours in an argon gas stream and further heated to 1,000° C. for 6 hours for calcination. After cooling, the contents of the crucible were withdrawn and subjected to measurements of the specific surface area SA (BET method), α-conversion (X-ray diffraction method) and median particle size $d_{50}$ (centrifugal precipitation method). Thus, it was found that the product had an SA of 20 (5) m²/g, an α-conversion of 95 (90)% and a $d_{50}$ of 0.2 (1) μ and no substantial coagulation by heating was observed. The numerical values given in the parentheses are those obtained when no resin was used.

The same tests were conducted using the foregoing gel to which 10 mg of α-alumina fine particles having a $d_{50}$ of 0.05μ was additionally added and it was found that the resulting product had an SA of 18 (3) m²/g, an α-conversion of 100 (95)% and a $d_{50}$ of 0.2 (1) μ. The numerical values given in the parentheses are those obtained when no resin was used.

2) 13 g of $AlCl_3.6H_2O$ was dissolved in 25 ml of water, 1 g of the sample resin was added thereto and uniformly mixed to give a gel as a whole and then 20 ml of a 28% aqueous solution of ammonia was added thereto. The gel originally transparent became opaque by the addition of the aqueous ammonia solution. The gel was then dried and introduced into an alumina crucible. The temperature of the dried gel was elevated to 1,000° C. over about 6 hours in an argon gas stream, and further heated for 6 hours for calcination. It was found that the product thus obtained had an SA of 95 m²/g and an α-conversion of 41%. The product was further heated at 1050° C. for 5 hours to give powder having an SA of 20 m²/g and an α-conversion of not less than 99% and a $d_{50}$ of 0.1μ.

3) An alumina sol was prepared by adding 1.6 g of behmite, 20 mg of α-alumina (d$_{50}$: 0.05μ) and 0.1 g of a 68% nitric acid solution to 18 ml of water, 1 g of the resin was added thereto and uniformly mixed to give a gel as a whole. The gel was then dried and introduced into an alumina crucible. The temperature of the dried gel was elevated to 1,000° C. over about 6 hours in an argon gas stream, and further heated for 6 hours for calcination. It was found that the product thus obtained had an SA of 39 (11) m$^2$/g, an α-conversion of 92 (80)% and a d$_{50}$ of 0.08 (1) μ.

4) To 7.1 g of a 20% SiO$_2$ colloidal solution was added 1 g of the resin, and the resulting mixture was uniformly mixed to give a gel as a whole. The gel was then dried and introduced into a silicon carbide crucible. The temperature of the dried gel was elevated to 1,500° C. over about 7 hours in an argon gas stream, and further heated for one hour for calcination. It was found that the product thus obtained had an SA of 10 (5) m$^2$/g, a fixed phase as determined by X-ray diffraction method: β-SiC single phase and a d$_{50}$ of 0.5 (1) μ.

5) A gel prepared in the same manner used in the example 3) was kneaded and extruded into a filament, through a needle having a diameter of about 700μ using a syringe, and the filament then dried and calcined in a muffle furnace maintained at 1,300° C. for about one minute in the air to give an alumina filament having a thickness of 200μ.

APPLICATION EXAMPLE 3

In general, the strength of concrete or mortar articles is greatly influenced by the water/cement ratio of the concrete or mortar composition. Namely, it is known that the smaller the amount of water, the higher the strength of the concrete or mortar observed after pouring and solidification. Nevertheless, the reduction of the water content leads to a lowering of the fluidity of the resulting cement composition, and thus to a reduction in the workability thereof at the job site, and therefore, the lower limit of the water/cement ratio is critical. A water reducing agent has been used to solve this problem, and this method makes it possible to increase the strength of the article to some extent, but not to that required. The excess water in the concrete or mortar composition is released on the surface of the poured concrete or mortar as bleeding water. For this reason, the strength of the resulting concrete or mortar article upwardly decreases, since the water/cement ratio is gradually increased towards the upper portion thereof. In addition, the subsequent process cannot be performed until the bleeding of water stops, and accordingly, this extends the term of the work. Under such circumstances, there has been proposed a method which comprises using an absorbing agent for removing the excess water, allowing the water-absorbing gel to gradually release the water in the concrete to thus cause internal wet-curing of the concrete, but the water-absorbing agents presently on the market do not absorb aqueous solutions containing ion components, to any great extent. In particular polyvalent ion components such as calcium ions, etc. do not ensure a required effect. On the other hand, the resin of the present invention can absorb even a saturated aqueous solution of calcium hydroxide, which is a principal component of the cement, as is clear from the foregoing absorption-quality Table 3, and can be used in the foregoing applications.

In addition, the cement composition in which the resin of the present invention is incorporated rarely allows a rapid drying out during curing, does not cause cracking due to the wet-curing effect, and has an improved strength and dimensional stability.

The resin of the present invention also may be used by forming an absorptive sheet from the resin and covering the poured concrete or mortar with the sheet, in addition to the incorporation of the resin into concrete or mortar compositions explained above. According to this method, the bleeding water is absorbed by the absorptive sheet and the strength of the poured concrete or mortar is improved due to the wet-curing effect, since the surface thereof comes into close contact with the absorptive sheet.

Moreover, if the mortar composition in which the resin of the present invention is incorporated is cured, the gelled portions in the cured mortar composition remains as voids and thus the density of the cured product can be reduced (formation of light weight mortar). On the contrary, the water-absorbing agents presently on the market absorb little of an aqueous solution containing polyvalent ion components, and thus the resulting mortar comprising such a water-absorbing agent contains only a small number of voids, and therefore, it is difficult to use the commercially available water-absorbing agents in the foregoing applications. In either of the foregoing cases, the desired effect can be ensured through the use of the resin of the present invention, which has an ability of absorbing a saturated aqueous solution of calcium hydroxide.

1) To a concrete composition which comprised 300 kg of Portland cement for general use (available from Nihon Cement Co., Ltd.), 225 kg of tap water, 670.6 kg of sand and 1031.1 kg of gravel, there was added 600 g each of the following sample resins (A), (B) and (C). Each concrete sample was prepared in accordance with JIS A 1138, "Method for Preparing Concrete in Laboratories" except that the time for kneading was changed to 4 minutes, the quantity of bleeding and the rate of bleeding of the resulting concrete samples were determined in accordance with JIS A 1123, and the compression strength thereof was determined in accordance with JIS A 1108. The results are summarized in the following Table 5.

Sample Resin:

A) crosslinked N-vinylacetamide polymer (average degree of polymerization of main chain: about 20,000; crosslinking agent: N,N'-1,4-butylenebis(N-vinylacetamide); crosslinking density: about 1/16,000)

B) crosslinked N-vinylacetamide/sodium acrylate polymer (molar ratio of the monomers: 50/50; average degree of polymerization of main chain: about 20,000; crosslinking agent: N,N'-1,4-butylenebis(N-vinylacetamide) and N,N'-methylenebisacrylamide; crosslinking density: about 1/17,000)

C) commercially available water absorptive resin "Sumicagel S-50"

The results observed when no resin was added are also listed in Table 5, as Comparative Example 1.

TABLE 5

| Resin | Rate of Bleeding (%) | Compression Strength (kgf/cm$^2$) | |
|---|---|---|---|
| | | After 7 Days | After 28 Days |
| A | 0.00 | 260 | 330 |
| B | 0.00 | 256 | 315 |
| C | 3.71 | 211 | 242 |

TABLE 5-continued

| Resin | Rate of Bleeding (%) | Compression Strength (kgf/cm²) After 7 Days | After 28 Days |
|---|---|---|---|
| Comp. Ex. 1 | 3.81 | 209 | 244 |

The bleeding of the concrete composition was clearly reduced and the compression strength thereof also improved through the incorporation of the resin of the present invention.

2) A mortar composition which comprised 3000 g of Portland cement for general use (available from Nihon Cement Co., Ltd.). 1500 g of tap water and 6000 g of sand was prepared and mixed and kneaded with 6.0 g each of the following sample resins (A), (B) and (C). The rate of change in length of the resulting mortar samples was determined in accordance with JIS A 1129. The results are summarized in the following Table 6.

Sample Resin:

A) crosslinked N-vinylacetamide polymer (average degree of polymerization of main chain: about 20,000; crosslinking agent: N,N'-1,4-butylenebis(N-vinylacetamide); crosslinking density: about 1/16,000)

B) crosslinked N-vinylacetamide/sodium acrylate polymer (molar ratio of monomers: 50/50; average degree of polymerization of main chain: about 20,000; crosslinking agent: N,N'-1,4-butylenebis(N-vinylacetamide) and N,N'-methylenebisacrylamide; crosslinking density: about 1/17,000)

C) commercially available water absorptive resin "Sumikagel S-50"

The results observed when no resin was added are also listed in Table 6, as Comparative Example 1.

TABLE 6

| Resin | Rate of Change in Length (×10⁻⁴) Storage Time: one week | Storage time: 4 weeks |
|---|---|---|
| A | −1.6 | −9.1 |
| B | −2.0 | −9.3 |
| C | −4.5 | −15.6 |
| Comp. Ex. 1 | −4.1 | −14.6 |

The rate of change in length was clearly reduced by the addition of the resin of the present invention.

3) Each of the following sample resins (A), (B) and (C) was uniformly sprayed on a nonwoven fabric in an amount of 26.5 g/m² and then another nonwoven fabric was put thereon. The surface of a poured concrete product was covered with this absorptive sheet to form a specimen. The concrete comprised 300 kg of Portland cement for general use (available from Nihon Cement Co., Ltd.), 225 kg of tap water, 670.6 kg of sand and 1031.1 kg of gravel and was prepared in accordance with JIS A 1138 with a slight modification. The sample was demolded on the material age of 7 days, the absorptive sheet was left as such, and the compression strengths at the material ages of 28 days and 91 days were determined in accordance with JIS A 1108. The results are summarized in the following Table 7.

Sample Resin:

A) crosslinked N-vinylacetamide polymer (average degree of polymerization of main chain: about 20,000; crosslinking agent: N,N'-1,4-butylenebis (N-vinylacetamide); crosslinking density: about 1/16,000)

B) crosslinked N-vinylacetamide/sodium acrylate polymer (molar ratio of monomers: 50/50; average degree of polymerization of main chain: about 20,000; crosslinking agent: N,N'-1,4-butylenebis (N-vinylacetamide) and N,N'-methylenebisacrylamide; crosslinking density: about 1/17,000)

C) commercially available water absorptive resin "Sumikagel S-50"

The results observed when no resin was added are also listed in Table 7, as Comparative Example 1.

TABLE 7

| Resin | Compression Strength (Kgf/cm²) After 28 days | After 91 days |
|---|---|---|
| A | 319 | 305 |
| B | 310 | 300 |
| C | 243 | 219 |
| Comparative Example 1 | 240 | 222 |

The compression strength of the concrete was clearly improved by the use of the absorptive sheet prepared by using the resin of the present invention.

4) A mortar composition which comprised 3000 g of Portland cement for general use (available from Nihon Cement Co., Ltd.), 1500 g of tap water and 6000 g of sand was prepared and mixed and kneaded with 12 g each of the following sample resins (A), (B) and (C). The density of the resulting mortar samples at the material age of 7 days was determined. The results are summarized in the following Table 8.

Sample Resin:

A) crosslinked N-vinylacetamide polymer (average degree of polymerization of main chain: about 20,000; crosslinking agent: N,N'-1,4-butylenebis (N-vinylacetamide); crosslinking density: about 16,000)

B) crosslinked N-vinylacetamide/sodium acrylate polymer (molar ratio of monomers: 50/50; average degree of polymerization of main chain: about 20,000; crosslinking agent: N,N'-1,4-butylenebis (N-vinylacetamide) and N,N'-methylenebisacrylamide; crosslinking density: about 1/17,000)

C) commercially available water absorptive resin "Sumikagel S-50"

The result observed when no resin was added is also listed in Table 8, as Comparative Example 1.

TABLE 8

| Resin | Density (g/cm³) |
|---|---|
| A | 1.83 |
| B | 1.71 |
| C | 2.03 |
| Comparative Example 1 | 2.04 |

The weight of the mortar clearly could be reduced by the addition of the absorbing agent of the present invention.

APPLICATION EXAMPLE 4

The resin of the present invention does not show a substantial reduction in the absorptivity of an aqueous solution containing a large amount of calcium ions, and accordingly, the moisture absorbent in which the resin of the present invention is incorporated can absorb a large amount of a solution resulting from the deliquescence of calcium chloride through moisture absorption, and the moisture absorbent as a whole loses its fluidity due to the gelation of the resin. As a result, the moisture absorbent does not cause a contamination of other substances. On the other hand, the conventional water-absorbing resins on the market have an extremely low rate of water absorptivity for an aqueous solution containing polyvalent ions, in particular calcium ions, and therefore, are not favorable for the foregoing applications. Representative examples thereof will be given below.

To 100 g of a pulverized product of calcium chloride which passed through a 200 mesh sieve was added 5, 10 or 50 g of the resin (A) of the present invention, and the resulting blends were mechanically mixed to give moisture absorbents 1, 2 and 3, respectively.

To 100 g of a pulverized product of calcium chloride which passed through a 200 mesh sieve was added 10 g of the resin (B) of the present invention, and the resulting blend was mechanically mixed to give a moisture absorbent 4.

To 100 g of a pulverized product of calcium chloride which passed through a 200 mesh sieve was added 50 g of the following resin (C), and the resulting blend was mechanically mixed to give a moisture absorbent 5.

A pulverized product per se of calcium chloride which passed through a 200 mesh sieve was used as a moisture absorbent 6.

50 g each of the moisture absorbents prepared above was allowed to stand in a thermo-hygrostat (temperature: 30° C.; humidity: 95%), the weight of each moisture absorbent after moisture absorption was determined, and the change in shape thereof was visually observed. The results are summarized in the following Table 9.

Sample Resin:

A) crosslinked N-vinylacetamide polymer (average degree of polymerization of main chain: about 20,000; crosslinking agent: N,N'-1,4-butylenebis (N-vinylacetamide); crosslinking density: about 16,000)

B) crosslinked N-vinylacetamide/sodium acrylate polymer (molar ratio of monomers: 50/50; average degree of polymerization of main chain: about 20,000; crosslinking agent: N,N'-1,4-butylenebis(N-vinylacetamide) and N,N'-methylenebisacrylamide; crosslinking density: about 1/17,000)

C) commercially available water absorptive resin "Diawet S-II"

TABLE 9

| | Moisture Absorbent | | | | | |
|---|---|---|---|---|---|---|
| | 1 | 2 | 3 | 4 | 5 | 6 |
| Weight Change | | | | | | |
| After 1 day | 102 | 101 | 131 | 103 | 100 | 97 |
| After 2 days | 132 | 133 | 146 | 132 | 131 | 128 |
| After 3 days | 148 | 145 | 170 | 149 | 146 | 147 |
| After 4 days | 165 | 166 | 189 | 170 | 168 | 169 |
| After 5 days | 188 | 186 | 214 | 191 | 187 | 185 |
| Moist. Abs. Ratio After 5 days (g/g) | 3.7 | 3.7 | 4.1 | 3.8 | 3.7 | 3.7 |
| Appearance After Moist. Abs. | jelly N.F. | jelly N.F. | jelly N.F. | jelly N.F. | liquid fluidity | liquid fluidity |

Moist. Abs.: moisture absorption.
N.F. no fluidity.

The moisture absorbent had clearly lost fluidity due to the addition of the resin of the present invention.

APPLICATION EXAMPLE 5

The resin of the present invention does not show any reduction in the rate of water absorptivity for body fluids such as urine and menstruous blood containing a large amount of salts, and thus can be used for making sanitary articles such as paper diapers and napkins.

The paper diaper in which the resin of the present invention is incorporated has a urine absorbing capacity higher than that of those containing a commercially available conventional water absorptive resin. As a result, the amount of the resin required for absorbing the same amount of urine can be substantially reduced, and thus the resin of the present invention is considered to be a body fluid absorbent favorable for the aforementioned applications.

A sanitary article essentially comprises 1) a liquid permeable top sheet, 2) an absorptive layer (such as polymeric absorbing member and cotton-like pulp) and 3) an air-permeable and waterproof sheet. Among these, the resin of the present invention is used in the absorptive layer. The absorptive layer may be prepared in a variety of forms, and typical examples thereof include those obtained by spraying the resin on a nonwoven fabric or by sandwiching the resin between nonwoven fabrics. The absorption ability of an article having a form similar thereto was determined. The absorption ability was determined as follows:

0.4 g each of the sample resins (A), (B), (C) and (D) was uniformly sprayed on a sheet of tissue paper having a size of 165×60 mm, then an additional sheet of tissue paper was put thereon and water was sprayed thereon while lightly pressing the assembly (the amount of water to be sprayed was properly determined). The assembly was pressed with emboss rollers heated to about 140° C. The resulting sheet was insufficiently dried after the treatment with the emboss rollers, and thus the sheet was additionally vacuum-dried at 80° C. for 2 hours. The dried sheet was placed on a wire cloth and dipped in an artificial urine maintained at 30° C. After one hour, the sheet was withdrawn from the artificial urine together with the wire cloth, drained by slanting the wire cloth at an angle of 45° for one minute, and then the weight of the sheet was determined. The results are listed in the following Table 10.

Sample Resin:

A) crosslinked N-vinylacetamide polymer (average degree of polymerization of main chain: about 20,000; crosslinking agent: N,N'-1,4-butylenebis (N-vinylacetamide); crosslinking density: about 1/16,000)

B) crosslinked N-vinylacetamide/sodium acrylate polymer (molar ratio of monomers: 50/50; average degree of polymerization of main chain: about 20,000; crosslinking agent: N,N'-1,4-butylenebis (N-vinylacetamide) and N,N'-methylenebisacrylamide; crosslinking density: about 1/17,000)

C) commercially available water absorptive resin "Sumikagel S-50"

D) commercially available water absorptive resin "Diawet S-II"

TABLE 10

| Sample Resin | Amount of Water Absorbed (g/sheet) |
|---|---|
| A | 22 |
| B | 38 |
| C | 18 |
| D | 14 |

We claim:

1. A liquid absorption agent for water or organic solvents comprising a crosslinked N-vinylcarboxylic acid amide resin comprising repeating units of the formula shown below, crosslinked with a crosslinking agent:

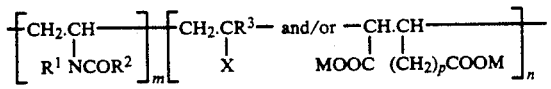

wherein $R^1$, $R^2$, and $R^3$ independently represent a hydrogen atom or methyl;

X represents a group —COOY, where Y represents a hydrogen atom, an alkali metal, a $C_1$–$C_6$ alkyl, or a lower alkyl substituted with a hydroxyl, a dialkylamino or a quaternary ammonium group; a group —CONHZ, where Z represents a hydrogen atom or a lower alkyl substituted with a dialkylamino group, a quaternary ammonium group, a sulfonic acid or an alkali metal salt thereof; a cyano, a 2-ketopyrrolidinyl, a lower alkoxy, a lower acyl, a lower acyloxy or a lower alkyl substituted with sulfonic acid or an alkali metal salt thereof, with a proviso that when $R^3$ is a methyl, X is not a cyano, a 2-ketopyrrolidinyl, a lower alkoxy, a lower acyl, a lower acyloxy and a lower alkyl substituted with sulfonic acid or a salt thereof;

M represents a hydrogen atom or an alkali metal;

p represents 0 or 1; and the molar ratio of m:n is 50–100:50–0, said crosslinking agent comprising, as an essential constituent, at least one compound selected from the group consisting of N,N'-α,ω-lower alkylenebis (N-vinylcarboxylic acid amides), N,N'-(diacetyl)-N,N'-(divinyl)-α,ω-diaminopolyethers and xylylene bis (N-vinylcarboxylic acid amides), the amount of the crosslinking agent being $2 \times 10^{-4}$ mol % to 0.2 mol %, based on the (co)polymerized component.

2. A liquid absorption agent as claimed in claim 1, wherein the average polymerization degree is 100 to 500,000 and the crosslinking density is 1/1000 to 1/500,000.

3. A liquid absorption agent as claimed in claim 1, wherein the crosslinking agent is at least one compound selected from the group consisting of N,N'-1,4-butylenebis(N-vinylacetamide), N,N'-1,6-hexylenebis(N-vinylacetamide), N,N-1,10-decylenebis(N-vinylacetamide), N,N'-3-oxa-1,5-pentylenebis(N-vinylacetamide), N,N'-3,6-dioxa-1,8-octylenebis(N-vinylacetamide), N,N'-p-xylylenebis(N-vinylacetamide), and N,N'-diacetyl-N,N'-divinyl-1,4-bisaminomethylcyclohexane.

4. A liquid absorption agent as claimed in claim 1, wherein the organic solvent is a single solvent having a solvent polarity parameter $E_T$ of 45 or more on a solvent mixture of a solvent polarity parameter $E_T$ of 43 or more.

5. A liquid absorption agent as claimed in claim 1, for use as a water retention or supply agent in a vegetative soil or an artificial medium.

6. A liquid absorption agent as claimed in claim 1, for use as a body fluid absorbent in sanitary articles.

7. A liquid absorption agent as claimed in claim 1, for use as an absorbent for water having a high calcium component for a concrete curing agent, cement modifier, or humectant.

8. A liquid absorption agent as claimed in claim 1, for use as a dispersing agent of a metal salt solution or a complex forming agent with metal compound.

* * * * *